United States Patent [19]
Kaneko et al.

[11] 3,935,268
[45] Jan. 27, 1976

[54] ω-[BIS(ω,ω-DIPHENYLALKYL)AMINO]ALKAN-1-OL AND THEIR SALTS

[75] Inventors: Hidehiko Kaneko, Minoo; Jiro Aritomi, Nara, both of Japan; Yuzuru Yamato, deceased, late of Minoo, Japan, by Akiko Yamato, Hiroshi Yamato, Yumi Yamato, heirs all of Minoo, Japan

[73] Assignee: Dainippon Pharmaceutical Co., Ltd., Osaka, Japan

[22] Filed: Aug. 30, 1972

[21] Appl. No.: 285,061

[52] U.S. Cl. ...... 260/570 R; 260/456 R; 260/456 P; 260/501.18; 260/501.19; 260/649 R; 424/316; 424/330
[51] Int. Cl.² ........................................ C07C 91/22
[58] Field of Search .......... 260/570, 501.18, 501.19; 424/330

[56] References Cited
OTHER PUBLICATIONS
Aritomi et al., "Yakugaku Zasshi," Vol. 91, No. 9, pp. 972–979 (1971).
Winthrop et al., "Journal Organic Chemistry," Vol. 27, pp. 230–241 (1962), pp. 230–231, 234 and 236.

*Primary Examiner*—Robert V. Hines
*Attorney, Agent, or Firm*—Jordan B. Bierman; Linda G. Bierman; Kenneth J. Stempler

[57] ABSTRACT

ω-[Bis(ω,ω-diphenylalkyl)amino]alkan-1-ol having the following formula:

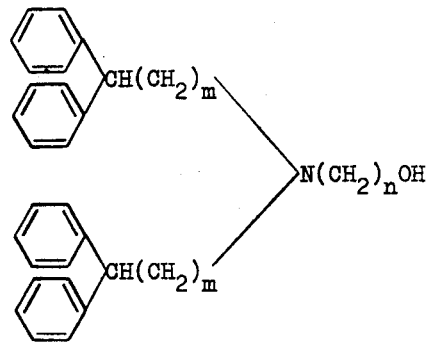

and their pharmaceutically acceptable acid addition salts which are useful for preventing and treating cerebral vascular diseases caused by cerebral blood flow disorder, processes for preparing the compounds and pharmaceutical compositions containing the compound.

3 Claims, No Drawings

ω-[BIS(ω,ω-DIPHENYLALKYL)AMINO]ALKAN-1-OL AND THEIR SALTS

The present invention relates to a compound having superior cerebral blood flow-increasing activity. More particularly, it relates to ω-[bis(ω,ω-diphenylalkyl)-amino]alkan-1-ol having the following formula:

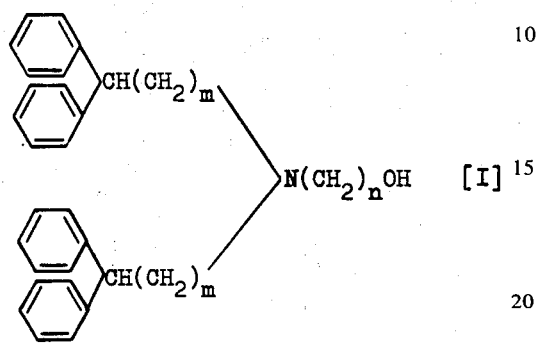

wherein $m$ is an integer of 1 to 3 and $n$ is an integer of 2 to 4, and their pharmaceutically acceptable acid addition salts, processes for the preparation thereof and pharmaceutical compositions containing the compound.

Hitherto, there have been studied many kinds of diphenylalkylamines and it has been known that some diphenylalkylamines possess superior pharmacological activities, such as antihistamine, parasympatholytic, antispasmodic or antipyretic activity.

There has been synthesized various kinds of diphenylalkylamine derivatives and studied the pharmacological properties thereof. It has now been found out that ω-[bis(ω,ω-diphenylalkyl)amino]alkan-1-ol and their pharmaceutically acceptable acid addition salts possess superior cerebral blood flow-increasing activity and are useful for preventing and treating cerebral vascular diseases caused by cerebral blood flow disorder.

An object of the present invention is to provide ω-[bis(ω,ω-diphenylalkyl)amino]alkan-1-ol and their pharmaceutically acceptable acid addition salts which are useful for preventing and treating cerebral vascular diseases caused by cerebral blood flow disorder.

Another object of the invention is to provide processes for the preparation of ω-[bis(ω,ω-diphenylalkyl)amino]alkan-1-ol and their pharmaceutically acceptable acid addition salts.

Further object of the invention is to provide a composition for preventing and treating cerebral vascural diseases caused by cerebral blood flow disorder containing the present compound set forth above as the essentially active ingredient.

Still further object of the invention is to provide a method for preventing and treating cerebral vascular diseases caused by cerebral blood flow disorder by administering the present compound set forth above to a patient.

These and other objects of the invention will be apparent from the description set forth hereinafter.

According to the present invention the present ω-[bis(ω,ω-diphenylalkyl)amino]alkan-1-ol and their pharmaceutically acceptable acid addition salts can be prepared by reacting ω,ω-diphenyl-1-substituted alkane with ω-aminoalkan-1-ol. The process can be illustrated by the following reaction scheme:

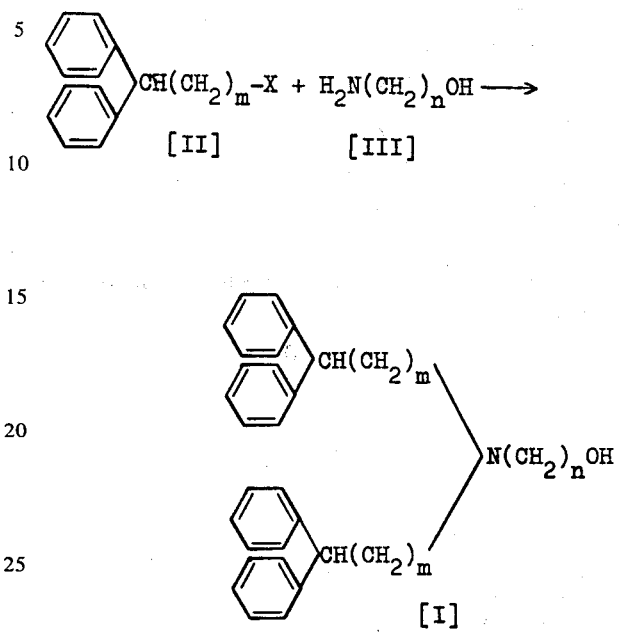

wherein $m$ and $n$ are the same as defined above, X is a halogen atom (e.g. Cl, Br or I) or a group of the formula: $-OSO_2R$ wherein R is a lower alkyl group having 1 to 3 carbon atoms (e.g. methyl, ethyl or propyl) or an aryl group (e.g. phenyl, tolyl, p-chlorophenyl or o-nitrophenyl).

In the above process, ω,ω-diphenyl-1-substituted alkane [II] can be readily reacted with ω-aminoalkan-1-ol [III] by heating a mixture thereof at a temperature of about 100 to about 200°C, preferably about 130° to about 160°C for a few to several hours in the presence or absence of an appropriate solvent (e.g. benzene, toluene, xylene or ethanol).

In this reaction it is preferable to use excess amounts of ω,ω-diphenyl-1-substituted alkane [II] or to add an excess of it in the way of the reaction for the purpose of minimizing the intermediate having the formula:

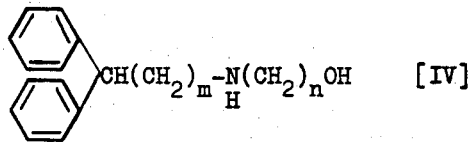

wherein $m$ and $n$ are the same as defined above.

Furthermore, the reaction is preferably carried out in the presence of an acid acceptor, such as an alkali metal carbonate (e.g. sodium carbonate or potassium carbonate) or an organic tertiary amine (e.g. trimethylamine, triethylamine or pyridine).

Alternatively, the present ω-[bis(ω,ω-diphenylalkyl)-amino]alkan-1-ol [I] and their pharmaceutically acceptable acid addition salts can be prepared by the reaction of bis(ω, ω-diphenylalkyl)amine with ω-haloalkan-1-ol which is illustrated by the following reaction scheme:

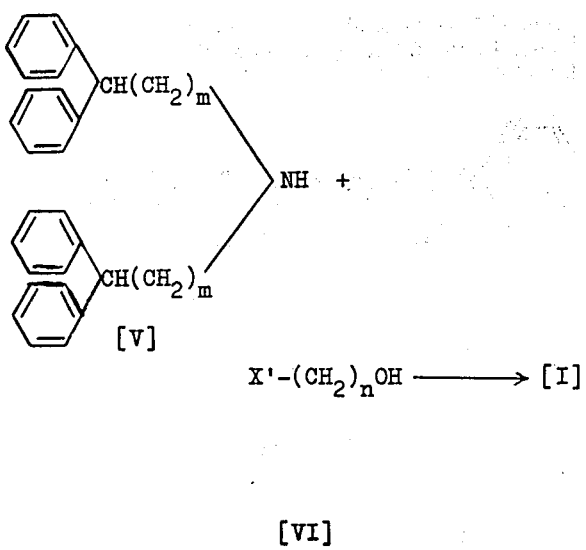

$$X'-(CH_2)_nOH \longrightarrow [I]$$

[VI]

wherein m and n are the same as defined above and X' is a halogen atom (e.g. Cl, Br or I).

In the above process, bis9ω,ω-diphenylalkyl)amine [V] can be readily reacted with ω-haloalkan-1-ol [VI] by heating a mixture thereof at a temperature of about 100° to about 200°C, preferably about 130° to about 160°C for a few to several hours in the presence or absence of an appropriate solvent (e.g. benzene, toluene, xylene or ethanol).

In the above processes, when the present compound [I] is obtained in the free form, it can be converted into its pharmaceutically acceptable acid addition salts by reacting with an inorganic acid (e.g. hydrochloric acid, hydrobromic acid, hydroiodic acid, sulfuric acid or nitric acid) or an organic acid (e.g. malonic acid, fumalic acid, maleic acid, oxalic acid, tartaric acid or methanesulfonic acid). On the other hand, when it is obtained in a form of salt, it can be converted into its free base by conventional method such as treatment with an alkaline substance (e.g. sodium hydroxide, potassium hydroxide, sodium carbonate, potassium carbonate, sodium bicarbonate or potassium bicarbonate).

Among the present compounds, 3-[bis(3,3-diphenylpropyl)amino]propan-1-ol has been described in Yakugaku Zasshi, Vol. 91, No. 9, pages 972–979, 1971. However, it has been merely described as a byproduct of other compounds and further any pharmacological activity of the present compound has not been described in the literature.

The present ω-[bis(ω,ω-diphenylalkyl)amino]alkan-1-ol and their pharmaceutically acceptable acid addition salts possess superior pharmacological activity, e.g. increasing cerebral blood flow and regional cerebral blood flow. Accordingly, the present compounds are useful for preventing and treating cerebral vascular diseases caused by cerebral blood flow disorder, such as cerebral infarction and transient cerebral ischemia.

The present compounds show low toxicity, and for instance, $LD_{50}$ of 3-[bis(3,3-diphenylpropyl)amino]propan-1-ol hydrochloride in mice was 44.6 mg/kg by intravenous injection and above 1000 mg/kg by oral administration.

The present ω-[bis(ω,ω-diphenylalkyl)amino]alkan-1-ol and their pharmaceutically acceptable acid addition salts can be administered orally or parenterally (e.g. intravenously) by conventional methods and with conventional pharmaceutical carriers in humans. They can be used in a form of tablets, capsules, powders or in a liquid form, such as solutions, emulsions, suspensions or syrups for oral administration, and in a form of solution in water, which is, if necessary, bufferred or made isotonic, for parenteral administration.

For the preparation of a solution or an injection of the present compounds, they are preferably dissolved in a mixed solvent of propyleneglycol-water or a aqueous solution of gluconic acid, lactobionic acid or a lactone of gluconic acid or lactobionic acid, by which the solubility of the present compounds can be increased.

The dosage per day of the present compounds for oral administration is within the range of about 0.2 to about 30 mg per kg of body weight, preferably within the range of about 0.5 to about 10 mg per kg of body weight, more particularly the range of about 1 to about 3 mg per kg of body weight. The dosage per day of the present compounds for intravenous injection is within the range of about 0.03 to about 10 mg per kg of body weight, preferably within the range of about 0.1 to about 3 mg per kg of body weight, more particularly the range of about 0.3 to about 1 mg per kg of body weight. Consequently, the present pharmaceutical composition contains the present compounds in the range of about 1.5 to about 1500 mg per daily dosage unit in adults, especially the range of about 10 to about 1500 mg per daily dosage unit for oral administration and the range of about 1.5 to about 500 mg per daily dosage unit for intravenous injection.

The preparation of the present ω-[bis(ω,ω-diphenylalkyl)amino]alkan-1-ol and their pharamceutically acceptable acid addition salts is set forth in the following Examples which are illustrative but not limiting.

EXAMPLE 1

A mixture of 3,3-diphenyl-1-chloropropane (8.5 g) and 3-aminopropan-1-ol (2.8 g) was heated with agitation at 150° to 160°C for 6 hours. After cooling, benzene (50 ml) was added to the reaction mixture and the solution was washed with 10 % hydrochloric acid and water in order. The benzene layer was dried over anhydrous sodium sulfate and evaporated under reduced pressure to give crystalline residue (5.0 g). The resultant residue was recrystallized from ethanol-ether to give 3-[bis(3,3-diphenylpropyl)amino]propan-1-ol hydrochloride (4.2 g). M.P. 152° to 153°C Anal. Calcd. for $C_{33}H_{37}NO.HCl$: C,79.25; H,7.66; N,2.80; Cl,7.09. Found: C,79.12; H,7.68; N,2.69; Cl,7.11.

In the same manner as described above, some other salts of the above compound were prepared by using acids listed below instead of hydrochloric acid:

A salt of sulfuric acid: M.P. 77° to 80°C. Anal. Calc. for $C_{33}H_{37}ON.1/2H_2SO_4 \cdot 2/3H_2O$: C,75.53; H,7.56; N,2.67; S,3.06. Found: C,75.40; H,7.35; N,2.64; S,3.27.

A salt of oxalic acid: M.P. 130° to 131°C. Anal. Calcd. for $C_{33}H_{37}ON.C_2H_2O_4$: C,75.92; H,7.10; N,2.53. Found: C,76.09; H,7,12; N,2.57.

A salt of tartaric acid: M.P. 138° to 140°C. Anal. Calcd. for $C_{33}H_{37}ON.1/2C_4H_6O_6$: C,78.04; H,7.48; N,2.60. Found: C,78.06; H,7.40; N,2.67.

A salt of methanesulfonic acid: M.P. 143° to 145°C. Anal. Calcd. for $C_{33}H_{37}ON.CH_3SO_3H$: C,72.95; H,7.38; N,2.50; S,5.73. Found: C,72.92; H,7,37; N,2.33; S,5.78.

EXAMPLE 2

A mixture of 3,3-diphenyl-1-chloropropane (10 g) and 2-aminoethan-1-ol (2.8 g) was heated with agitation at 135° to 145°C for 4 hours. After cooling, the reaction mixture was dissolved in chloroform (50 ml) and the solution was washed with 10 % hydrochloric acid and water in order. The chloroform layer was dried over anhydrous sodium sulfate and evaporated under reduced pressure to give crystalline residue (11 g). The resultant residue was recrystallized from ethanol-ether to give 2-[bis-(3,3-diphenylpropyl)-amino]ethan-1-ol hydrochloride (7.0 g). M.P. 146° to 148°C.

Anal. Calc. for $C_{32}H_{35}ON \cdot HCl$: C,79.07; H,7.47; N,2.88; Cl,7.29. Found: C,79.01; H,7.43; N,2.72; Cl,7.25

EXAMPLE 3

A mixture of 3,3-diphenylpropyl methanesulfonate (10 g), 3-aminopropan-1-ol (1.5 g) and anhydrous sodium carbonate (8 g) in xylene (100 ml) was heated at 135° to 145°C for 4 hours. After cooling, the reaction mixture was filtered and the filtrate was concentrated. To the resulting residue was added chloroform (100 ml). The solution was washed with 5 % hydrochloric acid and water in order, and the chloroform layer was dried over anhydrous sodium sulfate and evaporated. The resulting residue was crystallized from ether and then recrystallized from ethanolether to give 3-[bis(3,3-diphenylpropyl)amino]propan-1-ol hydrochloride (4.0 g). M.P. 152° to 154°C.

EXAMPLE 4

In the same manner as described in Example 3,3,3-diphenylpropyl para-toluenesulfonate (10 g) was reacted with 3-aminopropan-1-ol (1.2 g) to give 3-[bis(3,3-diphenylpropyl)amino]propan-1-ol hydrochloride (3.5 g). M.P. 152° to 154°C.

EXAMPLE 5

A mixture of 3,3-diphenylpropyl methanesulfonate (10 g), 2-aminoethan-1-ol (1.2 g) and anhydrous sodium carbonate (8 g) in xylene (50 ml) was heated at 135° to 145°C for 4 hours. After cooling, the reaction mixture was filtered and the filtrate was concentrated. To the resulting residue was added chloroform (100 ml). The solution was washed with 5 % hydrochloric acid and water in order, and the chloroform layer was dried over anhydrous sodium sulfate and evaporated. The resulting residue was crystallized from ether and then recrystallized from ethanolether to give 2-[bis(3,3-diphenylpropyl)amino]ethan-1-ol hydrochloride (6.8 g). M.P. 146° to 148°C.

EXAMPLE 6

In the same manner as described in Example 5, 3,3-diphenylpropyl para-toluenesulfonate (10 g) was reacted with 2-aminoethan-1-ol (1.0 g) in xylene (50 ml) in the presence of anhydrous sodium carbonate (8 g) to give 2-[bis(3,3-diphenylpropyl)amino]ethan-1-ol hydrochloride (5.0 g). M.P. 146° to 148°C.

EXAMPLE 7

To bis(3,3-diphenylpropyl)amine (1.2 g) was added 3-chloropropan-1-ol (20 ml) and the mixture was heated with agitation at 150° to 160°C for 4 hours. The reaction mixture was evaporated under reduced pressure, and to the resulting residue was added benzene (20 ml). The mixture was washed with 5% hydrochloric acid and water in order. The benzene layer was dried over anhydrous sodium sulfate and evaporated under reduced pressure to give oily residue. The residue thus obtained was crystallized from acetone-petroleum ether and further recrystallized from ethanol-ether to give 3-[bis(3,3-diphenylpropyl)amino]propan-1-ol hydrochloride (0.5 g). M.P. 152° to 154°C.

The starting bis(3,3-diphenylpropyl)amine used in the above method was prepared as follows:

A mixture of 3,3-diphenylpropylamine (4.9 g) and 3,3-diphenyl-1-chloropropane (5.0 g) in xylene (10 ml) was heated at 120° to 130°C for 4 hours. After cooling, a small amount of benzene was added to the reaction mixture and then the mixture was filtered to remove 3,3-diphenylpropylamine hydrochloride. The filtrate was washed with 5 % hydrochloric acid and water in order. The organic layer was dried over anhydrous sodium sulfate and evaporated under reduced pressure. The resulting crystalline residue was recrystallized from methanol to give bis(3,3-diphenylpropyl)amine hydrochloride (3.0 g.). M.P. 192° to 194°C.

Anal. Calcd. for $C_{30}H_{31}N \cdot HCl$: C,81.55; H,7.24; N,3.17; Cl,8.03. Found: C,81.65; H,7.53; N,3.01; Cl,8.19.

EXAMPLE 8

To bis(3,3-diphenylpropyl)amine (3 g) was added ethylene chlorohydrin (60 ml) and the mixture was heated with agitation at 130° to 140°C for 4 hours. The reaction mixture was evaporated to remove unreacted ethylene chlorohydrin, and to the resulting residue was added benzene (50 ml). The mixture was washed with 5 % hydrochloric acid and water in order. The benzene layer was dried over anhydrous sodium sulfate and evaporated under reduced pressure to give oily residue (3.5 g). The residue thus obtained was crystallized from acetone-petroleum ether and further recrystallized from ethanol-ether to give 2-[bis(3,3-diphenylpropyl)amino]ethan-1-ol hydrochloride (2.0 g). M.P. 146° to 148°C.

3-[Bis(3,3-diphenylpropyl)amino]propan-1-ol hydrochloride and 2-[bis(3,3-diphenylpropyl)amino]ethan-1-ol hydrochloride prepared in accordance with the foregoing procedure were administered to laboratory test animals following established procedures and were found to exhibit unexpected and desirable pharmacological properties. The following Examples are representative of such determinations. In the Examples, papaverine hydrochloride and cinnarizine hydrochloride (1-cinnamyl-4-diphenylmethylpiperazine hydrochloride) being a kind of diphenylalkylamine derivative, which have been used as a cerebral vasodilator, were used as controls.

EXAMPLE 9

Effect on carotid artery blood flow:

To study the effect of 3-[bis(3,3-diphenylpropyl)amino]propan-1-ol hydrochloride and 2-[bis(3,3-diphenylpropyl)amino]ethan-1-ol hydrochloride on carotid artery blood flow, 3 dogs of either sex, weighing 16 – 20 kg, were used.

The electric magnetic flow meter (Nihonkoden, MF-5) was placed on the left common carotid artery. Femoral artery blood flow was also measured with the flow meter and systemic blood pressure in the right femoral artery was recorded with the pressure transducer (Nihonkoden, MP-4T), simultaneously. The results are shown in Table I.

diphenylpropyl)amino]ethan-1-ol hydrochloride, but it increased femoral artery blood flow in the same way as papaverine.

Table I

| Drug | Dose (mg/kg. iv) | Heart rate (beats/min) | | | | Systemic artery blood pressure (mmHg) | | | |
|---|---|---|---|---|---|---|---|---|---|
| | | Before | After | (%) | Duration (min) | Before | After | (%) | Duration (min) |
| Papaverine | 0.03 | 150 | 153 | 2 | 0.5 | 128 | 123 | −4 | 0.7 |
| | 0.10 | 150 | 158 | 5 | 0.9 | 127 | 118 | −7 | 1.0 |
| | 0.30 | 152 | 180 | 18 | 1.2 | 128 | 107 | −16 | 1.3 |
| Cinnarizine | 0.03 | 151 | 151 | 0 | 0 | 128 | 125 | −3 | 0.2 |
| | 0.10 | 154 | 158 | 3 | 0.8 | 130 | 124 | −5 | 1.8 |
| | 0.30 | 150 | 158 | 5 | 3.2 | 129 | 98 | −24 | 3.5 |
| 3-[bis(3,3-diphenylpropyl)-amino]propan-1-ol hydrochloride | 0.03 | 147 | 147 | 0 | 0 | 117 | 116 | 0 | 0.4 |
| | 0.10 | 152 | 157 | 3 | 1.0 | 115 | 111 | −4 | 2.4 |
| | 0.30 | 155 | 167 | 8 | 2.7 | 117 | 105 | −10 | 2.8 |
| 2-[bis(3,3-diphenylpropyl)-amino]ethan-1-ol hydrochloride | 0.03 | 139 | 139 | 0 | 0 | 116 | 114 | −3 | 0.3 |
| | 0.10 | 145 | 148 | 2 | 1.4 | 116 | 110 | −5 | 2.3 |
| | 0.30 | 148 | 161 | 9 | 2.0 | 114 | 103 | −10 | 4.2 |

| Drug | Carotid artery blood flow (ml/min) | | | | Femoral artery blood flow | | | |
|---|---|---|---|---|---|---|---|---|
| | Before | After | (%) | Duration (min) | Before | After | (%) | Duration (min) |
| Papaverine | 124 | 136 | 10 | 0.7 | 45 | 49 | 9 | 0.8 |
| | 126 | 181 | 44 | 0.9 | 43 | 59 | 37 | 1.2 |
| | 122 | 232 | 90 | 1.4 | 43 | 82 | 91 | 1.7 |
| Cinnarizine | 120 | 128 | 7 | 1.0 | 44 | 48 | 9 | 0.6 |
| | 116 | 129 | 11 | 1.0 | 43 | 52 | 21 | 0.8 |
| | 115 | 162 | 41 | 2.7 | 44 | 58 | 32 | 3.0 |
| 3-[bis(3,3-diphenylpropyl)-amino]propan-1-ol hydrochloride | 131 | 145 | 11 | 0.9 | 45 | 49 | 9 | 0.6 |
| | 137 | 176 | 29 | 1.6 | 42 | 46 | 10 | 2.1 |
| | 133 | 195 | 47 | 2.7 | 38 | 45 | 18 | 3.1 |
| 2-[bis(3,3-diphenylpropyl)-amino]ethan-1-ol hydrochloride | 126 | 132 | 5 | 0.8 | 43 | 45 | 5 | 0.8 |
| | 125 | 166 | 33 | 2.1 | 40 | 44 | 10 | 2.5 |
| | 125 | 188 | 50 | 2.9 | 42 | 49 | 17 | 3.4 |

As shown in Table I, when 3-[bis(3,3-diphenylpropyl)amino]propan-1-ol hydrochloride and 2-[bis(3,3-diphenylpropyl)amino]ethan-1-ol hydrochloride were injected intravenously in a dose of 0.03 mg/kg or more, carotid artery blood flow increased, but the rate of increase in femoral artery blood flow was not so significant.

Papaverine increased carotid and femoral artery blood flow at the same extent, but the duration of the effect was short in comparison with 3-[bis(3,3-diphenylpropyl)amino]propan-1-ol hydrochloride and 2-[bis(3,3-diphenylpropyl)amino]ethan-1-ol hydrochloride. Cinnarizine also increased carotid artery blood flow similar to 3-[bis(3,3-diphenylpropyl)amino]propan-1-ol hydrochloride and 2-[bis(3,3-

EXAMPLE 10

Effect on regional cerebral blood flow

To study the effect of 3-[bis(3,3-diphenylpropyl)amino]propan-1-ol hydrochloride and 2-[bis(3,3-diphenylpropyl)amino]ethan-1-ol hydrochloride on regional cerebral blood flow, 5 dogs of either sex, weighing 9 – 12 kg, were used.

The thermo couples (Shinei, P-6 & AWN-500) were placed on gyrus suprasylvius of cortex and hippocampus for measurement of the regional cerebral blood flow. At the same time, systemic blood pressure and carotid artery blood flow were recorded. The results are shown in Table II.

Table II

| Drug | Dose (mg/kg, iv) | Heart rate beats/min | | | | Systemic artery blood pressure (mmHg) | | | |
|---|---|---|---|---|---|---|---|---|---|
| | | Before | After | (%) | Duration (min) | Before | After | (%) | Duration (min) |
| Papaverine | 0.03 | 128 | 138 | 7.8 | 0.5 | 122 | 116 | −4.9 | 0.8 |
| | 0.10 | 116 | 128 | 10.3 | 1.2 | 119 | 106 | −10.9 | 1.3 |
| | 0.30 | 132 | 154 | 16.7 | 1.7 | 131 | 113 | −13.7 | 1.9 |
| Cinnarizine | 0.03 | 120 | 120 | 0 | 0 | 135 | 129 | −4.4 | 2.0 |
| | 0.10 | 129 | 131 | 1.6 | 1.5 | 141 | 133 | −5.7 | 3.2 |
| | 0.03 | 116 | 122 | 5.2 | 2.8 | 129 | 115 | −10.9 | 4.0 |
| 3-[bis(3,3-diphenyl-propyl)amino]propan-1-ol hydrochloride | 0.03 | 138 | 138 | 0 | 0 | 118 | 116 | −1.7 | 1.2 |
| | 0.10 | 143 | 148 | 3.5 | 2.1 | 125 | 112 | −10.4 | 2.2 |
| | 0.30 | 129 | 136 | 5.4 | 3.8 | 129 | 108 | −16.3 | 3.9 |
| 2-[bis(3,3-diphenyl-propyl)amino]ethan-1-ol hydrochloride | 0.03 | 122 | 122 | 0 | 0 | 155 | 155 | 0 | 0 |
| | 0.10 | 132 | 135 | 2.3 | 1.4 | 149 | 144 | −3.4 | 3.0 |
| | 0.30 | 128 | 137 | 7.0 | 3.1 | 145 | 134 | −7.6 | 4.3 |

Table II-continued

| Drug | Carotid artery blood flow (ml/min) | | | | Regional cerebral blood flow (cortex) (μV) | | | | Regional cerebral blood flow (hippocampus) (μV) | | | |
|---|---|---|---|---|---|---|---|---|---|---|---|---|
| | Before | After | (%) | Duration (min) | Before | After | (%) | Duration (min) | Before | After | (%) | Duration (min) |
| Papaverine | 62 | 66 | 6.5 | 0.8 | 124 | 128 | 3.2 | 0.7 | 129 | 135 | 4.7 | 1.2 |
| | 68 | 80 | 17.6 | 1.2 | 110 | 119 | 8.2 | 1.3 | 131 | 145 | 10.7 | 1.7 |
| | 75 | 114 | 52.0 | 1.6 | 129 | 148 | 14.7 | 1.6 | 137 | 162 | 18.2 | 2.4 |
| Cinnarizine | 70 | 76 | 8.6 | 1.0 | 110 | 117 | 6.4 | 2.4 | 122 | 127 | 4.1 | 0.8 |
| | 56 | 67 | 19.6 | 2.1 | 115 | 128 | 11.3 | 2.8 | 114 | 127 | 11.4 | 2.0 |
| | 77 | 109 | 41.6 | 2.9 | 114 | 144 | 26.3 | 3.1 | 115 | 138 | 20.0 | 3.0 |
| 3-[bis(3,3-diphenyl-propyl)amino]propan-1-ol hydrochloride | 52 | 56 | 7.6 | 1.2 | 116 | 122 | 5.2 | 1.1 | 141 | 145 | 2.8 | 1.2 |
| | 68 | 84 | 23.5 | 1.8 | 125 | 145 | 16.0 | 1.7 | 128 | 142 | 10.9 | 1.9 |
| | 64 | 92 | 43.5 | 3.6 | 118 | 156 | 32.2 | 3.4 | 132 | 160 | 21.2 | 3.7 |
| 2-[bis(3,3-diphenyl-propyl)amino]ethan-1-ol hydrochloride | 37 | 40 | 8.1 | 1.0 | | | | | 155 | 164 | 5.8 | 1.2 |
| | 47 | 56 | 19.1 | 2.0 | | | | | 127 | 140 | 10.2 | 2.1 |
| | 46 | 62 | 34.8 | 3.7 | | | | | 144 | 172 | 19.4 | 3.6 |

As shown in Table II, when 3-[bis(3,3-diphenylpropyl)amino]propan-1-ol hydrochloride was injected intravenously in a dose of 0.03 mg/kg or more, the regional cerebral blood flow was increased at the sites of cortex and hippocampus. 2-[Bis(3,3-diphenylpropyl)amino]ethan-1-ol hydrochloride was also increased the regional cerebral blood flow at the site of hippocampus.

tension, 7 dogs of either sex, weighing 10 – 12 kg, were used.

The oxygen electrode was placed by the side of the thermo couple which was set on cortex and measured by electric oxygraph polarographically. At the same time, systemic blood pressure, carotid artery blood flow and regional cerebral blood flow (at the site of cortex) were measured. The results are shown in Table III.

Table III

| Drug | Dose (mg/kg, iv) | Heart rate (beats/min) | | | | Systemic artery blood pressure (mmHg) | | | |
|---|---|---|---|---|---|---|---|---|---|
| | | Before | After | (%) | Duration (min) | Before | After | (%) | Duration (min) |
| Papaverine | 0.03 | 123 | 130 | 5.7 | 0.6 | 127 | 121 | −4.7 | 1.2 |
| | 0.10 | 126 | 134 | 6.3 | 1.3 | 135 | 115 | −14.8 | 1.8 |
| | 0.30 | 119 | 137 | 15.1 | 2.0 | 126 | 95 | −24.6 | 3.1 |
| Cinnarizine | 0.03 | 127 | 127 | 0 | 0 | 144 | 144 | 0 | 0 |
| | 0.10 | 131 | 133 | 1.5 | 0.8 | 140 | 134 | −4.3 | 2.3 |
| | 0.30 | 118 | 126 | 6.8 | 2.1 | 134 | 123 | −8.2 | 3.5 |
| 3-[bis(3,3-diphenyl-propyl)amino]propan-1-ol hydrochloride | 0.03 | 129 | 129 | 0 | 0 | 125 | 121 | −3.2 | 1.8 |
| | 0.10 | 130 | 133 | 2.3 | 1.5 | 126 | 114 | −9.5 | 2.5 |
| | 0.30 | 126 | 131 | 4.0 | 2.1 | 131 | 113 | −13.7 | 3.6 |

| Drug | Carotid artery blood flow (ml/min) | | | | Regional cerebral blood flow (cortex) (μV) | | | | Regional cerebral oxygen tension (cortex) ($\times 10^{+8}$Amp) | | | |
|---|---|---|---|---|---|---|---|---|---|---|---|---|
| | Before | After | (%) | Duration (min) | Before | After | (%) | Duration (min) | Before | After | (%) | Duration (min) |
| Papaverine | 72 | 80 | 11.1 | 1.1 | 114 | 119 | 4.4 | 0.9 | 19.7 | 19.7 | 0 | 0 |
| | 83 | 108 | 30.1 | 1.4 | 110 | 117 | 6.4 | 1.5 | 22.3 | 23.4 | 4.9 | 2.0 |
| | 68 | 112 | 64.7 | 1.8 | 119 | 133 | 11.8 | 2.1 | 18.5 | 20.0 | 8.1 | 4.5 |
| Cinnarizine | 61 | 66 | 8.2 | 0.9 | 116 | 122 | 5.2 | 1.6 | 20.5 | 20.9 | 2.0 | 1.8 |
| | 57 | 65 | 14.0 | 1.7 | 125 | 139 | 11.3 | 2.4 | 18.3 | 20.7 | 13.1 | 3.2 |
| | 60 | 81 | 35.0 | 2.6 | 106 | 130 | 22.6 | 3.1 | 22.2 | 26.5 | 19.4 | 3.5 |
| 3-[bis(3,3-diphenyl-propyl)amino]propan-1-ol hydrochloride | 55 | 60 | 9.1 | 1.3 | 113 | 123 | 8.8 | 1.7 | 21.5 | 21.9 | 1.9 | 1.7 |
| | 65 | 80 | 23.1 | 2.1 | 115 | 135 | 17.5 | 2.6 | 18.3 | 20.9 | 14.2 | 2.2 |
| | 59 | 85 | 44.1 | 3.9 | 122 | 161 | 32.2 | 4.0 | 17.9 | 22.4 | 25.1 | 5.3 |

Papaverine increased the regional blood flow in the site of hippocampus, but the rate of increase in the site of cortex was not so significant. And the effect of papaverine in the site of hippocampus was weak as compared with 3-[bis(3,3-diphenylpropyl)amino]propan-1-ol hydrochloride and 2-[bis(3,3-diphenylpropyl)amino]ethan-1-ol hydrochloride. Cinnarizine increased the regional blood flow in the sites of cortex and hippocampus.

EXAMPLE 11

Effect on the regional cerebral oxygen tension

To study of 3-[bis(3,3-diphenylpropyl)amino]propan-1-ol hydrochloride on the regional cerebral oxygen As shown in Table III, when 3-[bis(3,3-diphenylpropyl)amino]propan-1-ol hydrochloride was injected intravenously in a dose of 0.10 mg/kg or more, the regional oxygen tension of cortex was increased in proportion to the increase of regional blood flow.

The effect of papaverine on regional cerebral oxygen tension was pretty weak as compared with 3-[bis(3,3-diphenylpropyl)amino]propan-1-ol hydrochloride. Cinnarizine increased the regional oxygen tension with the increase of regional blood flow, but the effect of cinnarizine was a little weak in comparison with 3-[bis(3,3-diphenylpropyl)amino]propan-1-ol hydrochloride.

What is claimed is:

1. ω-[Bis(ω,ω-diphenylalkyl)amino]alkan-1-ol of the formula:
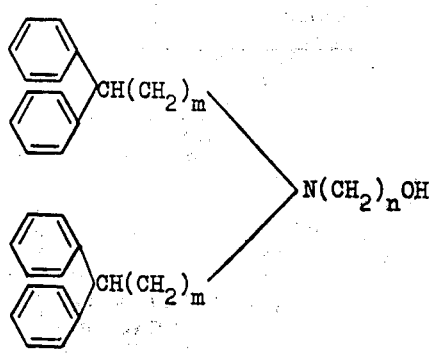
wherein $m$ is 2 and $n$ is 2 or 3 and the pharmaceutically acceptable acid addition thereof.
2. 3-[Bis(3,3-diphenylpropyl)amino]propan-1-ol and its pharmaceutically acceptable acid addition salt.
3. 2-[Bis(3,3-diphenylpropyl)amino]ethan-1-ol and its pharmaceutically acceptable acid addition salt.
* * * * *